United States Patent [19]

Brockway et al.

[11] Patent Number: 4,684,344
[45] Date of Patent: Aug. 4, 1987

[54] ELECTRICALLY POWERED AND HEATED ENDODONTIC SYRINGE

[75] Inventors: Charles E. Brockway, Palatine; John J. Saeli, Wheaton, both of Ill.

[73] Assignee: Nalge Company, Rochester, N.Y.

[21] Appl. No.: 850,469

[22] Filed: Apr. 11, 1986

[51] Int. Cl.4 .............................................. A61C 5/02
[52] U.S. Cl. .................................................... 433/81
[58] Field of Search .................... 604/72, 403; 433/80, 433/81, 82, 83, 84, 85, 86, 87, 88, 89

[56] References Cited

U.S. PATENT DOCUMENTS 2,691,374 10/1954 McKibbin et al. ..................... 604/72
4,582,488 4/1986 Newman ............................... 433/81

Primary Examiner—Robert Peshock
Attorney, Agent, or Firm—Marjama & Pincelli

[57] ABSTRACT

An endodontic syringe for injecting thermoplastic material, such as gutta percha into a root canal cavity. The syringe includes a drive motor and mechanism for reversible axial translation of a plunger, a removable gutta percha cartridge and needle, and a heating element surrounding the cartridge to heat the gutta percha to a fluid condition. Forward movement of the plunger, against a piston within the cartridge, ejects gutta percha for the cartridge and needle. Reverse movement of the plunger returns it to its starting position, at which the used cartridge can be removed and replaced.

The cartridge and needle are of aluminum or aluminum alloy.

1 Claim, 4 Drawing Figures

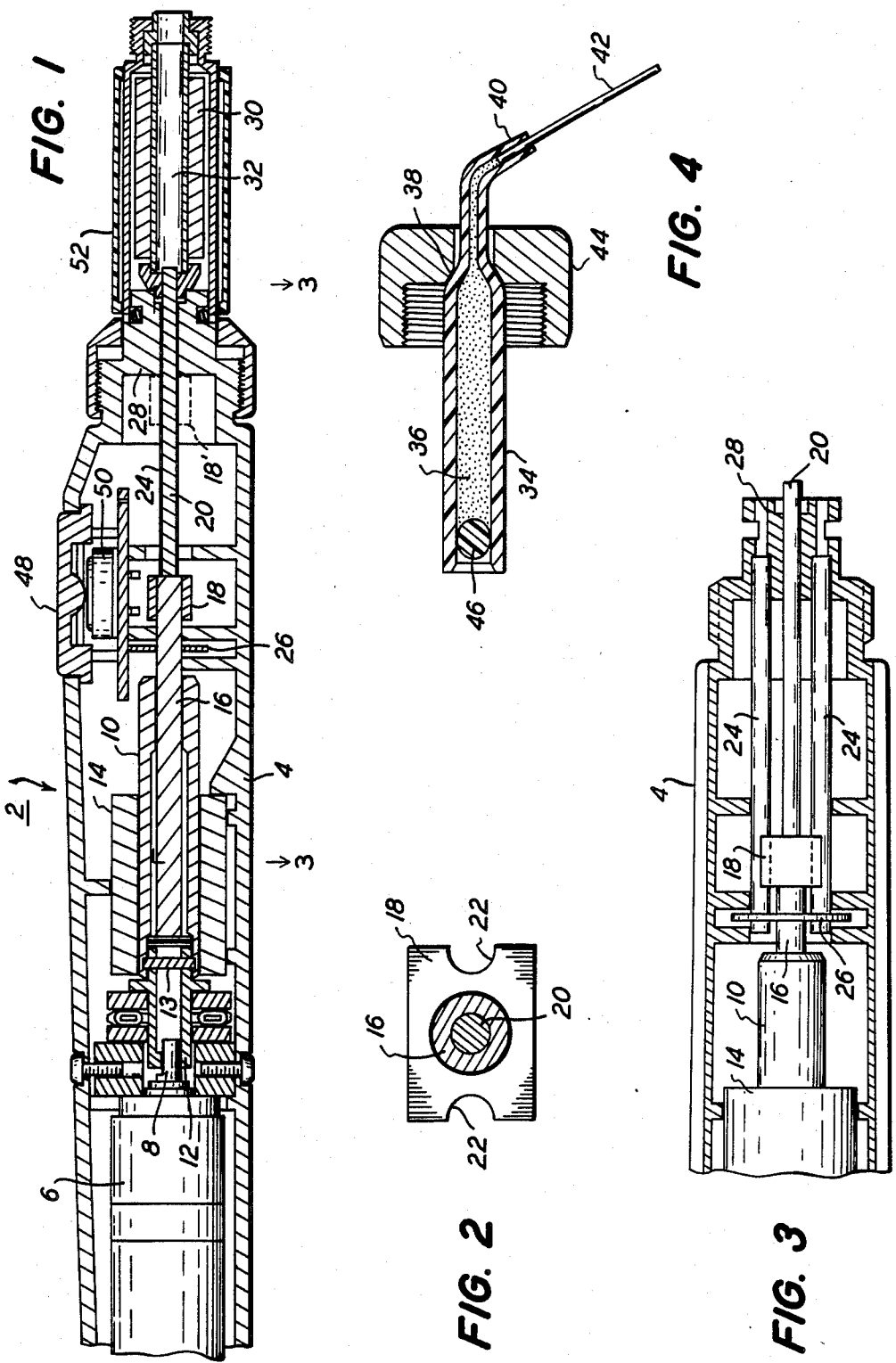

ELECTRICALLY POWERED AND HEATED ENDODONTIC SYRINGE

BACKGROUND OF THE INVENTION

This invention relates to an electrically driven and electrically heated endodontic syringe for extruding heated thermoplastic material through a needle into a tooth root canal cavity.

Historically, dental root canal cavities have long been filled with gutta percha, a gum obtained by boiling the sap of certain species of trees particularly native to Borneo, New Guinea, and Malaya. The procedure has for a long time been a hand operation in which slender needle-shaped "points" of gutta percha are pushed and packed into the root canal cavity by hand tools.

More recently there have been some advances in the art, particularly in terms of mechanization. While some synthetic materials for this use have been devised, gutta percha remains the standard and favorite. It is desirable, in order to do the best job of filling any cavity, to fill it with liquid rather than to pack it with a solid. With gutta percha, this presents problems. It must be heated to approximately 230° F. in order to flow freely into fine spaces or through a fine orifice. In order to mechanize the extrusion of gutta percha through a needle and into a root canal cavity, not only must the body or reservoir of gutta percha be heated, but the gutta percha must also be maintained at elevated temperature through the length of the needle.

U.S. Pat. No. 4,265,618 to Herskovitz et al discloses one apparatus in which this problem has been addressed. In Herskovitz et al, a hand-held syringe includes a cylindrical electrical heater into which a rod of gutta percha is placed. A needle of copper or silver extends from the heater body. The gutta percha is heated within the cylindrical heater, then pushed out of the heater, by means of a manual plunger rod, through the copper or silver needle. The needle, by virtue of its high thermal conductivity, is said to conduct enough heat from the heater body to keep the gutta percha in a fluid condition throughout the length of the needle. Copper or silver was considered necessary in Herskovitz et al because of the required length of the needle, and the needle in turn is of such required length to enable the user to put proper bends in it for use. It is not clear, but it appears that in the use of this device, when the procedure is completed the user must somehow flush the needle of remaining gutta percha, perhaps by pushing boiling water through it, to prevent its being permanently clogged.

SUMMARY AND OBJECTS OF THE INVENTION

Objects of the present invention include the provision of a mechanized endodontic syringe in which the consumable material is easily placed in the apparatus in cartridge form, the cartridge including a needle of such relatively economical material that both cartridge and needle are disposable after use.

The invention is practised, and these objects realized, in one form by an endodontic syringe having a drive motor, a plunger, and a heating element all axially disposed on a handpiece. The heating element surrounds a cartridge chamber into which is removably mounted a gutta percha cartridge, the cartridge having a needle extending from it. Cartridge and needle are of aluminum or aluminum alloy and are heated by conduction from the heating element. A preformed bend in the needle minimizes its required length.

DRAWING

FIG. 1 is a side sectional view of an endodontic syringe of the present invention.

FIG. 2 is an axial view of a yoke member 18, shown in side view in FIG. 1.

FIG. 3 is a cutaway view taken generally along the line 3—3 of FIG. 1.

FIG. 4 is a sectional view of a removable cartridge for attachment to the right end of the device of FIG. 1.

DESCRIPTION

Referring to FIG. 1, a handpiece is generally indicated at 2 and includes an elongated housing 4 in which is mounted a reversible electric motor 6 with a rotor shaft 8. A driving nut 10 is mounted for rotation with the rotor shaft 8 by means of a bearing sleeve 12 which is keyed to shaft 8 by means of a flat on the shaft and a mating flat in the aperture of the bearing sleeve. Bearing sleeve 12 and driving nut 10 are joined by a pin 13. Nut 10 is rotatably mounted within a cylindrical bearing 14.

A translation screw 16 is threaded within the driving nut 10. A yoke 18 is fixed at the end of translation screw 16, forward of the nut 10. A plunger rod 20 is in turn fixed to and extends axially forward of the yoke 18. Screw 16, yoke 18, and rod 20 are non-rotating.

Yoke 18 is seen in axial view (somewhat enlarged) in FIG. 2 which shows a recess 22 on each of its sides. FIG. 3, which is rotated 90° from FIG. 1, shows a pair of longitudinal guide rails 24 suitably fixed within the housing 4 and extending from a guide-rail support plate 26 to the end of housing 4. Yoke 18, by means of its recesses 22, is slidable along the guide rails 24 and is restrained from rotation by guide rails 24.

Rotation of the motor 6 and its rotor shaft 8, in a first direction of rotation, rotates the driving nut 10 which in turn causes the non-rotating translation screw 16, with yoke 18 and plunger rod 20, to move forward toward a limit position of yoke 18 indicated in phantom at 18'. The reverse direction of rotation of motor 6 pulls the translation screw rearward toward its home position.

At the right end of the handpiece 2, an electrical heater 30 is mounted within the housing. Heater 30 is preferably cylindrical and surrounds a cartridge chamber 32. At the extreme right end of the handpiece 2, the housing 4 is threaded to receive a mating retaining nut.

FIG. 4 shows a cartridge 34, preferably of circular cross-section, for insertion into the cartridge chamber 32. Cartridge 34 is a hollow member having an internal cavity 36 to contain thermoplastic material, such as gutta percha. Cartridge 34 has a shoulder 38, forward of which the outside and inside diameters of the cartridge are reduced to form a discharge nipple 40. A hollow discharge needle 42 extends from the nipple 40. Nipple 40 and needle 42 are together bent to an angle relative to the long axis of the handpiece to permit easy insertion into a tooth root canal. The angle of bend shown in the drawing is approximately 60° from the long axis. An apertured retaining nut 44 slips over the needle 42 and nipple 40 and abuts against the shoulder 38 of the cartridge 34. The cartridge 34 is insertable into the cartridge chamber 32 defined by the heater 30, and is held securely in place by retaining nut 44 which threads onto the housing 4.

Cartridge 34 is formed of cold drawn and swaged aluminum or, preferably, aluminum alloy designated 6061 having a thermal conductivity of approximately 97 Btu/hr/ft$^2$/°F./ft. Needle 42 is preferably of the same material. Retaining nut 44 is of a plastic material, preferably polysulfone, which is of low thermal conductivity and is autoclavable at 300°–400° F.

The cartridge cavity 36 contains thermoplastic material, more specifically gutta percha. A piston 46 is placed in the rearward end of the cavity 36. Piston 46 is preferably of a deformable material, such as Teflon, and of a spherical shape prior to its insertion into the cavity. Upon insertion it is slightly deformed or flattened as shown so as to form a good sealing relationship with the wall of cavity 36. The cartridge 34 with needle 42 and piston 46 are intended to be disposable when the cavity has been emptied of gutta percha. Simple removal of the retaining nut 44 permits the user to remove the cartridge 34 and replace it with another. The retaining nut 44 is retained as a permanent part of the handpiece.

A push button 48 on the handpiece housing 4 is operatively connected to a switch 50, within the housing, which is in turn a part of appropriate circuitry connected to the motor 6 to energize the motor in both forward and reverse directions of rotation and to deenergize the same. The details of the circuitry are straightforward, and are not considered essential to an understanding of the present invention.

An easily removable heat shield 52 fits over the heater portion of the handpiece to protect the patient. The heat shield is removable for cleaning and autoclaving.

OPERATION

From an initial or starting condition shown in FIG. 1, with the translation.screw 16, yoke 18, and plunger rod 20 in their home position, the actuation of switch 50 and motor 6 provides rotation of the rotor shaft 8 and driving nut 10 in their "forward" direction of rotation. This in turn causes the non-rotating translation screw 16, yoke 18, and plunger rod 20 to translate to the right, or "forward", against the piston 46 to eject gutta percha from the cartridge 34 and through the needle 42. Until the yoke 18 reaches its limit position at 18', repeated breaking and making of this electrical circuit by means of the switch 48 will repeatedly stop and start the motor in the same direction of rotation. When the limit position 18' is reached, the circuitry will reverse the motor rotation and the entire plunger apparatus will return to its home position. The empty cartridge can then be removed and a new one put in place.

What is claimed is:

1. An endodontic syringe for injecting a heated thermoplastic material into a root canal cavity, including:
   a drive motor mounted on a handpiece,
   a plunger operatively connected to said drive motor for reversible axial translation into and out of a cartridge chamber defined by said handpiece,
   a heating element disposed on said handpiece about said cartridge chamber,
   a cartridge composed of aluminum or an aluminum alloy removably mounted within said cartridge chamber in axial alignment with said plunger, said cartridge defining an elongated cavity with a discharge orifice at the discharge end of said cavity, said cartridge including a piston disposed in said cavity, said cartridge adapted to contain a quantity of said thermoplastic material within said cavity between said piston and said discharge orifice, and
   a hollow dispensing needle composed of aluminum or an aluminum alloy extending from said discharge orifice.

* * * * *